US006734962B2

(12) United States Patent
Treado et al.

(10) Patent No.: US 6,734,962 B2
(45) Date of Patent: May 11, 2004

(54) NEAR INFRARED CHEMICAL IMAGING MICROSCOPE

(75) Inventors: Patrick J. Treado, Pittsburgh, PA (US); Matthew Nelson, Pittsburgh, PA (US); Scott Keitzer, Export, PA (US)

(73) Assignee: ChemImage Corporation, Pittsburgh, PA (US)

( * ) Notice: Subject to any disclaimer, the term of this patent is extended or adjusted under 35 U.S.C. 154(b) by 201 days.

(21) Appl. No.: 09/976,391

(22) Filed: Oct. 12, 2001

(65) Prior Publication Data

US 2002/0113210 A1 Aug. 22, 2002

Related U.S. Application Data

(60) Provisional application No. 60/239,969, filed on Oct. 13, 2000.

(51) Int. Cl.[7] .................................................. G01J 3/44
(52) U.S. Cl. .................. 356/301; 356/51; 356/326; 356/331; 250/339.05
(58) Field of Search .................. 356/301, 51, 310, 356/326, 328, 330–334, 73; 250/339.05, 339.02, 339.01, 339.07, 339, 458.1, 459.1, 461.1, 462.2; 382/284

(56) References Cited

U.S. PATENT DOCUMENTS

| | | | | |
|---|---|---|---|---|
| 5,194,912 A | | 3/1993 | Batchelder et al. | 356/301 |
| 5,377,003 A | | 12/1994 | Lewis et al. | 356/300 |
| 5,377,004 A | | 12/1994 | Owen et al. | 356/301 |
| 5,442,438 A | | 8/1995 | Batchelder et al. | 356/301 |
| 5,493,443 A | * | 2/1996 | Simon et al. | 359/368 |
| 5,528,393 A | | 6/1996 | Sharp et al. | 359/53 |
| 5,623,342 A | | 4/1997 | Baldwin et al. | 356/301 |
| 5,689,333 A | | 11/1997 | Batchelder et al. | 356/301 |
| 5,710,626 A | | 1/1998 | O'Rourke et al. | 356/301 |
| 5,862,273 A | | 1/1999 | Pelletier | 385/12 |
| 5,901,261 A | | 5/1999 | Wach | 385/38 |
| 5,911,017 A | | 6/1999 | Wach et al. | 385/12 |
| 5,943,122 A | * | 8/1999 | Holmes | 356/73 |
| 6,002,476 A | | 12/1999 | Treado et al. | 356/301 |
| 6,088,100 A | * | 7/2000 | Brenan et al. | 356/346 |
| 6,483,641 B1 | * | 11/2002 | MacAulay | 359/385 |
| 6,571,117 B1 | * | 5/2003 | Marbach | 600/473 |

OTHER PUBLICATIONS

H. Skinner, T. Cooney, S. Sharma and S. Angel. "Remote Raman Microimaging Using an AOTF and a Spatially Coherent Microfiber Optical Probe". vol. 50 *Applied Spectroscopy* No. 8, pp. 1007–1014 (1996).

I. Lewis and P. Griffiths, "Raman Spectrometry with Fiber–Optic Sampling", vol. 50 *Applied Spectroscopy*, No. 10, pp. 12A–29A (1996).

Patrick J. Treado, Ira W. Levin, and E. Neil Lewis, Indium Antimonide (InSb) Focal Plane Array (FPA) Detection for Near–Infrared Imaging Microscopy. Applied Spectroscopy 48. (1994) 607.

(List continued on next page.)

*Primary Examiner*—Frank G. Font
*Assistant Examiner*—Layla Lauchman
(74) *Attorney, Agent, or Firm*—Buchanan Ingersoll, P.C.

(57) ABSTRACT

A chemical imaging system is provided which uses a near infrared radiation microscope. The system includes an illumination source which illuminates an area of a sample using light in the near infrared radiation wavelength and light in the visible wavelength. A multitude of spatially resolved spectra of transmitted, reflected, emitted or scattered near infrared wavelength radiation light from the illuminated area of the sample is collected and a collimated beam is produced therefrom. A near infrared imaging spectrometer is provided for selecting a near infrared radiation image of the collimated beam. The filtered images are collected by a detector for further processing. The visible wavelength light from the illuminated area of the sample is simultaneously detected providing for the simultaneous visible and near infrared chemical imaging analysis of the sample. Two efficient means for performing three dimensional near infrared chemical imaging microscopy are provided.

16 Claims, 6 Drawing Sheets

OTHER PUBLICATIONS

Treado et al. "A Thousand Points of Light: The Hadamard Transform" *Analytical Chemistry* 61 (1989) Jun. 1, No. 11, pp 723–734.

P. Treado et al., "High–Fidelity Raman Imaging Spectrometry: A Rapid Method Using an Acousto–Optic Tunable Filter". vol. 46 *Applied Spectroscopy*, No. 8, pp. 1211–(1992).

H. Morris, C. Hoyt, P. Miller and P. Treado, "Liquid Crystal Tunable Filter Raman Chemical Imging", vol. 50 *Applied Spectroscopy*, No. 6, pp. 805–811 (1996).

Patrick J. Treado, Ira W. Levin and E. Neil Lewis, Near–Infrared Acousto–Optic Filtered Spectroscopic Microscopy: A Solid–State Approach to Chemical Imaging, Applied Spectroscopy 46, (1992) 553–559.

Patrick J. Treado and Michael D. Morris, Infrared and Raman Spectroscopic Imaging (Marcell Decker, New York, 1992) pp. 71–108.

John F. Turner H and Patrick J. Treado, LCTF Raman Chemical Imaging in the Near–Infrared, Proc. SPIE 3061, (1997) 280–283.

Spectral Dimensions. NIR Systems Product Information, http://www.spectraldimensions.com/products/b–nir.html.

* cited by examiner

A

B

C

NEAR INFRARED CHEMICAL IMAGING MICROSCOPE

This application claims the benefit of U.S. Provisional Application No. 60/239,969, entitled "Near Infrared Chemical Imaging Microscope" filed Oct. 13, 2000.

This work is supported by the National Institute of Standards and Technology (NIST) under the Advanced Technology Program (ATP) award (Contract Number 70NANB8H4021)

FIELD OF INVENTION

The present invention is related to near-infrared (NIR) microscopes for spectroscopic and image analysis, and, in particular, to microscopes useful for both NIR spectroscopy, NIR chemical imaging and NIR volumetric chemical imaging.

BACKGROUND OF THE INVENTION

NIR spectroscopy is a mature, non-contact, non-destructive analytical characterization tool that has been widely applied to a broad range of materials. The NIR region of the electromagnetic spectrum encompasses radiation with wavelengths of 0.78 to 2.5 $\mu$m (12,800 to 4,000 cm$^{-1}$). NIR spectra result from the overtone and combination bands of fundamental mid-infrared (MIR) bands. Among the many desirable characteristics, NIR is used to rapidly obtain both qualitative and quantitative information about the molecular makeup of a material. Digital imaging, on the other hand, provides a means to obtain optical (i.e., spatial—morphological, topographical, etc.) information about a material. By combining the spatial information obtained from digital imagery and the spectral information obtained from NIR spectroscopy, the chemical makeup of complex material matrices can be mapped out in both two and three spatial dimensions. NIR chemical imaging combines NIR spectroscopy and digital imaging for the molecular-specific analysis of materials. A NIR chemical imaging microscope apparatus employing NIR absorption molecular spectroscopy for materials characterization is disclosed.

State-of-the-Art Instrumentation

NIR microscopes are used to obtain NIR absorption, transmittance or reflectance spectra (e.g., NIR microspectra) from samples ranging in size between 1 and 1000 $\mu$m. These instruments are typically equipped with a digital camera to visually locate a region of interest on a sample upon which a NIR light beam from a Fourier transform (FT) spectrometer is focused. Reflective optics are used to direct the transmitted or reflected light from the sample to a NIR detector. The output is a NIR absorption spectrum collected in transmittance or reflectance mode.

NIR chemical imaging can be considered an extension of NIR microspectroscopy. Much of the imaging performed since the development of the first NIR microprobes has involved spatial scanning of samples beneath NIR microscopes in order to construct NIR "maps" of surfaces. In point by point scanning with NIR microscopes, the NIR light beam is focused onto the surface of a sample or apertured to illuminate a small region of a sample and a spectrum from each spatial position is collected. Images are obtained by rastering the sample through the focused or apertured NIR light beam and the spectra recorded are then reconstructed to form an image. Although point scanning produces images based on NIR contrast, long experimental times are common since the duration of the experiment is proportional to the number of image pixels. As a direct result, point scan images are captured at low image definition, which relates directly to the limited utility of the technique as an imaging tool for the routine assessment of material morphology. The spatial resolution of the image is limited by the size of the NIR illumination spot on the sample (no less than 1 $\mu$m) and the rastering mechanism, which requires the use of moving mechanical parts that are challenging to operate reproducibly.

NIR imaging cameras have been used in photography for decades. Until recently, however, it has not been easily accessible to those not versed in traditional photographic processes. By using optical filters (e.g., cold filters) that block the visible wavelengths (0.4–0.78 $\mu$m), charge-coupled devices (CCDs) used in digital cameras and camcorders can be used to sense NIR light out to around 1100 nm. Other regions of the NIR spectrum can be viewed using devices such as indium gallium arsenide (InGaAs—0.9 $\mu$m to 1.7 $\mu$m) and indium antimonide (InSb—1.0 $\mu$m to 5.0 $\mu$m) focal plane array (FPA) detectors. These integrated wavelength NIR imaging approaches allow one to study relative light intensities of objects over broad ranges of the NIR spectrum, but useful chemical information is unattainable without the use of some type of discrete wavelength filtering device.

The use of dielectric interference filters in combination with NIR FPAs is one method in which chemical information can be obtained from a sample. To form NIR chemical images, a NIR light beam is defocused to illuminate a wide field of view and the reflected or transmitted light from the illuminated area is imaged onto a two-dimensional NIR detector. A selection of discrete dielectric interference filters provided in a filter wheel, or a linearly variable or circularly variable format can be positioned in front of a broadband NIR light source, or in front of the NIR FPA itself in order to collect NIR wavelength resolved images. Typically, the use of several fixed bandpass filters is required to access the entire NIR spectrum. The spatial resolution of the NIR image approaches that of the optical microscope, while spectral resolution of several nanometers has been demonstrated. Key limitations of the dielectric filter approach include the need for a multitude of discrete filters to provide appreciable free spectral range, or the reliance on moving mechanical parts in employing continuously tunable dielectric interference filters as a requirement to form wavelength resolved images. While moving mechanical assemblies can be engineered they add cost and complexity to NIR chemical imaging systems. Alternatives to moving mechanical assemblies are generally more cost effective and provide performance advantages.

Acousto-optic tunable filters (AOTFs) have been employed as no-moving-parts imaging spectrometers for NIR imaging. The AOTF is a solid-state device that is capable of functioning from the UV to the mid-IR depending on the choice of the filter's crystal material. Operation of the AOTF is based on the interaction of light with a traveling acoustic sound wave in an anisotropic crystal medium. The incident light is diffracted with a narrow spectral bandpass when an rf signal is applied to the device. By changing the applied rf frequency under computer control the spectral passband can be tuned rapidly with the benefit of non-moving parts.

For use in NIR chemical imaging, AOTFs have distinct limitations. AOTFs have imaging performance that is degraded appreciably from diffraction-limited conditions due to dispersion effects and image shifting effects. Furthermore, AOTFs suffer from temperature instability and exhibit nonlinear properties that complicate their use as imaging spectrometers.

An aim of NIR chemical imaging technology development has been to develop a NIR imaging technique that combines diffraction-limited spatial resolution with high spectral resolution. NIR chemical imaging techniques have only recently achieved a degree of technological maturity that allow the collection of high resolution (spectral and spatial) data with the advent of the liquid crystal (LC) imaging spectrometers. In general, LC devices provide diffraction-limited spatial resolution. The spectral resolution of the LC imaging spectrometer is comparable to that provided by dispersive monochromator and Fourier transform interferometers. In addition, LC technology provides high out of band rejection, broad free spectral range, moderate transmittance, high overall etendue and highly reproducible random access computer controlled tuning.

Under normal NIR imaging operation, LC imaging spectrometers allow NIR chemical images of samples to be recorded at discrete wavelengths (energies). A spectrum is generated corresponding to thousands of spatial locations at the sample surface by tuning the LC imaging spectrometer over a range of wavelengths and collecting NIR images systematically. Contrast is generated in the images based on the relative amounts of NIR absorption, transmittance or reflectance that is generated by the different species located throughout the sample. Since a high quality NIR spectrum is generated for each pixel location, a wide variety of chemometric analysis tools, both univariate and multivariate, can be applied to the NIR image data to extract pertinent information. Correlative multivariate routines are particularly powerful when applied to chemical images collected from samples intentionally seeded with a known standard material. This approach of incorporating calibration standards within an image field of view can be extended to quantitative chemical image analysis. In addition, digital image analysis procedures can also be applied to high image quality NIR chemical images to perform routine particle analysis in both two (2D) and three (3D) spatial dimensions. Volumetric 3D NIR chemical image analysis can be performed very effectively using numerical deconvolution computational strategies.

SUMMARY OF THE INVENTION

To address the need for a device that can provide video imaging, NIR spectroscopy and high resolution (spatial and spectral) NIR chemical imaging in two and three spatial dimensions, a novel NIR chemical imaging microscope has been developed that is NIR chemical imaging capable.

The microscope design uses NIR optimized liquid crystal (LC) imaging spectrometer technology for wavelength selection. The NIR optimized refractive microscope is used in conjunction with infinity-corrected objectives to form the NIR image on the detector with or without the use of a tube lens. An integrated parfocal analog color CCD detector provides real-time sample positioning and focusing. The color image and the NIR image are fused in software. In one configuration, the NIR microscope may be used as a volumetric imaging instrument through the means of moving the sample through focus, collecting images at varying focal depths and reconstructing a volumetric image of the sample in software, or through the means of keeping the sample fixed and changing the wavelength dependent depth of penetration in conjunction with a refractive tube lens with a well characterized chromatic effect. The output of the microscope can be coupled to a NIR spectrometer either via direct optical coupling or via a fiber optic. A Chemical Imaging Addition Method seeds the sample with a material of known composition, structure and/or concentration and then generates the NIR image suitable for qualitative and quantitative analysis. The microscope generates NIR chemical image data that is analyzed and visualized using chemical image analysis software in a systematic and comprehensive manner. While this invention has been demonstrated on a microscope optic platform, the novel concepts are also applicable to other image gathering platforms, namely fiberscopes, macrolens systems and telescopes.

DETAILED DESCRIPTION OF THE INVENTION

The NIR chemical imaging microscope combines in a single platform a NIR optimized refractive optical microscope base, which is equipped with NIR optimized infinity-corrected microscope objectives, an automated XYZ translational microscope stage and quartz tungsten halogen (QTH) lamps to secure and illuminate samples for NIR spectroscopy and imaging, an analog color charge-coupled device (CCD) detector for ordinary optical image collection and digital image collection, a NIR LC imaging spectrometer for NIR chemical image wavelength selection and a room temperature or optionally cooled NIR FPA for NIR image capture.

Figure 1:
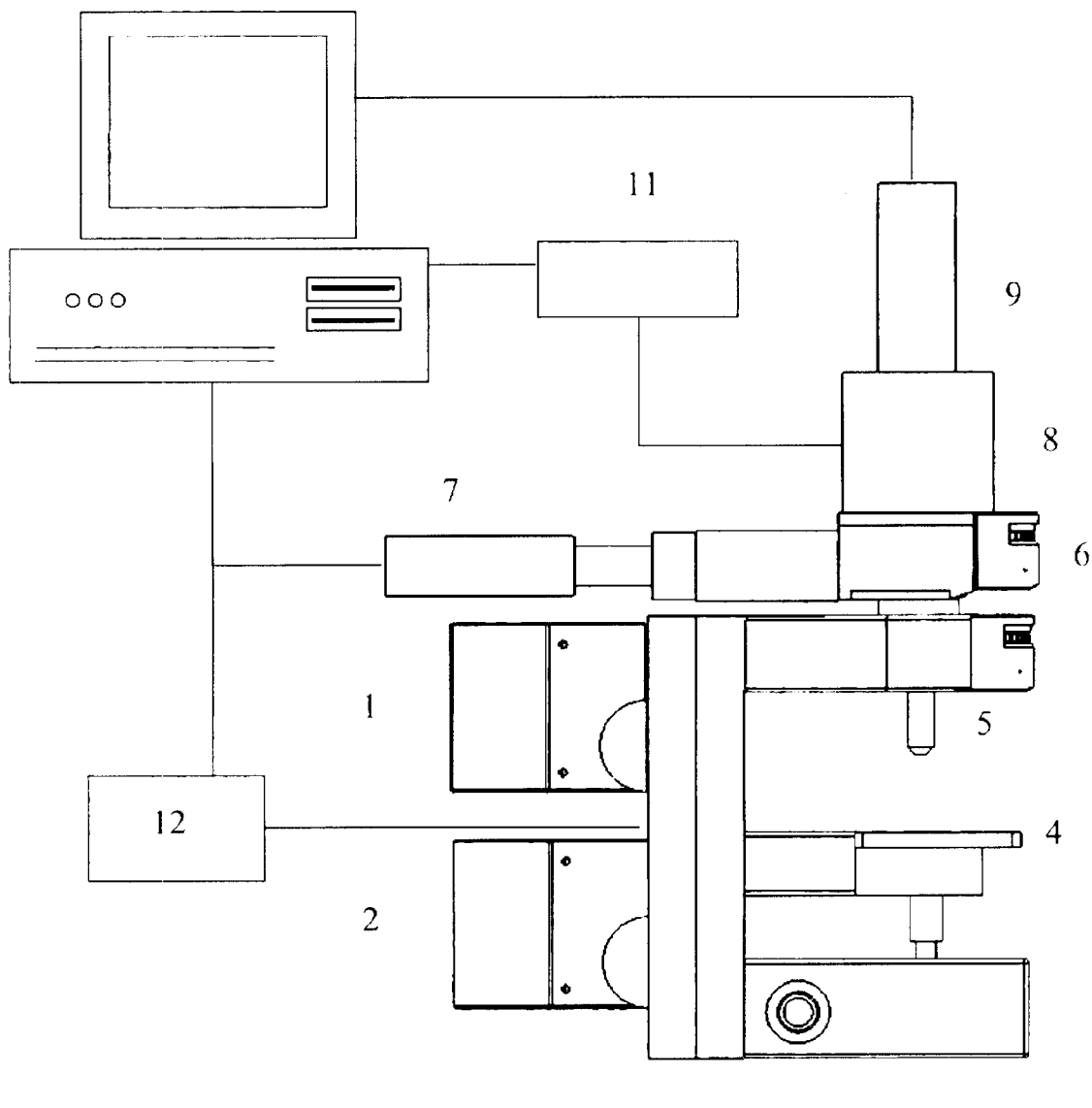
FIG. 1 shows a schematic diagram of the near-infrared (NIR) chemical imaging microscope

FIG. 1 is a schematic diagram of the NIR chemical imaging microscope. NIR illumination is directed to the sample in a reflected light configuration using a QTH source or other broadband white light source, including metal halide or Xe arc lamps 1 or a transmitted light configuration using QTH or suitable NIR source 2 of an NIR optimized refractive optical microscope platform 3. The reflected or transmitted NIR light is collected from the sample positioned on the automated XYZ translational microscope stage 4 through an infinity-corrected NIR optimized microscope objective 5.

Ordinary optical imagery of the sample can be obtained using a mirror or beamsplitter or prism arrangement inserted into turret 6 and collecting an image with an analog or digital color or monochrome charge-coupled device (CCD) or CMOS detector 7. In NIR chemical imaging mode, the magnified NIR image is coupled through a NIR LC imaging spectrometer 8 and collected on a room temperature or cooled NIR focal plane array (FPA) detector 9. The FPA is typically comprised of indium gallium arsenide (InGaAs), but may be comprised of other NIR sensitive materials, including platinum silicide (PtSi), indium antimonide (InSb) or mercury cadmium telluride (HgCdTe). Using a beam-splitting element inserted into turret 6, NIR and ordinary optical imagery can be collected with an analog monochrome or color CCD detector 7 and NIR FPA 9 simultaneously.

A central processing unit 10, typically a Pentium computer, is used for NIR chemical image collection and processing. The analog color CCD 7, NIR FPA 9, automated XYZ translational microscope stage 4 controlled via a controller 12 and NIR LC imaging spectrometer 8 (through LC imaging spectrometer controller 11) are operated with commercial software, such as Acquisition Manager (Chemlcon Inc.) in conjunction with ChemImage (Chemlcon Inc.).

By introducing a polarization sensitive beam splitting element in the optical path prior to the NIR LC imaging spectrometer 8 (not shown in schematic diagram), a portion of the NIR light from the sample may be coupled to a remote NIR spectrometer (also not shown in schematic diagram).

Preferably, NIR optimized liquid crystal (LC) imaging spectrometer technology is used for wavelength selection. The LC imaging spectrometer may be of the following types: Lyot liquid crystal tunable filter (LCTF); Evans Split-Element LCTF; Solc LCTF; Ferroelectric LCTF; Liquid crystal Fabry Perot (LCFP); or a hybrid filter technology comprised of a combination of the above-mentioned LC filter types or the above mentioned filter types in combination with fixed bandbass and bandreject filters comprised of dielectric, rugate, holographic, color absorption, acousto-optic or polarization types.

One novel component of this invention, is that a NIR optimized refractive microscope is used in conjunction with infinity-corrected objectives to form the NIR image on the detector without the use of a tube lens. The microscope can be optimized for NIR operation through inherent design of objective and associated anti-reflective coatings, condenser and light source. To simultaneously provide high numerical apertures the objective should be refractive. To minimize chromatic aberration, maximize throughput and reduce cost the conventional tube lens can be eliminated, while having the NIR objective form the NIR image directly onto the NIR focal plane array (FPA) detector, typically of the InGaAs type. The FPA can also be comprised of Si, SiGe, PtSi, InSb, HgCdTe, PdSi, Ge, analog vidicon types. The FPA output is digitized using an analog or digital frame grabber approach.

An integrated parfocal analog CCD detector provides real-time sample positioning and focusing. An analog video camera sensitive to visible radiation, typically a color or monochrome CCD detector, but may be comprised of a CMOS type, is positioned parfocal with the NIR FPA detector to facilitate sample positioning and focusing without requiring direct viewing of the sample through conventional eyepieces. The video camera output is typically digitized using a frame grabber approach.

The color image and the NIR image are fused using software. While the NIR and visible cameras often generate images having differing contrast, the sample fields of view can be matched through a combination of optical and software manipulations. As a result, the NIR and visible images can be compared and even fused through the use of overlay techniques and correlation techniques to provide the user a near-real time view of both detector outputs on the same computer display. The comparitive and integrated views of the sample can significantly enhance the understanding of sample morphology and architecture. By comparing the visible, NIR and NIR chemical images, additional useful information can be acquired about the chemical composition, structure and concentration of species in samples.

The NIR microscope can be used as a volumetric imaging instrument through the means of moving the sample through focus in the Z, axial dimension, collecting images in and out of focus and reconstructing a volumetric image of the sample in software. For samples having some volume (bulk materials, surfaces, interfaces, interphases), volumetric chemical imaging in the NIR has been shown to be useful for failure analysis, product development and routine quality monitoring. The potential also exists for performing quantitative analysis simultaneous with volumetric analysis. Volumetric imaging can be performed in a non-contact mode without modifying the sample through the use of numerical confocal techniques, which require that the sample be imaged at discrete focal planes. The resulting images are processed and reconstructed and visualized. Computional optical sectioning reconstruction techniques based on a variety of strategies have been demonstrated, including nearest neighbors and iterative deconvolution.

An alternative to sample positioning combined with computation reconstruction is to employ a tube lens in the image formation path of the microscope which introduces chromatic aberration. As a result the sample can be interrogated as a function of sample depth by exercising the LC imaging spectrometer, collecting images at different wavelengths which penetrate to differing degrees into bulk materials. These wavelength dependent, depth dependent images can be reconstructed to form volumetric images of materials without requiring the sample to be moved, again through application of computational optical sectioning reconstruction algorithms.

The output of the microscope can be coupled to a NIR spectrometer either via direct optical coupling or via a fiber optic cable. This allows conventional spectroscopic tools to be used to gather NIR spectra for traditional, high speed spectral analysis. The spectrometers can be of the following types: fixed filter spectrometers; grating based spectrometers; Fourier Transform spectrometers; or Acousto-Optic spectrometers.

A novel method that is readily employed by the disclosed microscope invention is a method described as the Chemical Imaging Addition Method which involves seeding the sample with a material of known composition, structure and/or concentration and then generating the NIR image suitable for qualitative and quantitative analysis. The Chemical Imaging Addition Method is a novel extension of a standard analytical chemical analysis technique, the Standard Addition Method. A common practice in quantitative chemical analysis is to construct a standard calibration curve which is a plot of analytical response for a particular technique as a function of known analyte concentration. By measuring the analytical response from an unknown sample, an estimate of the analyte concentration can then be extrapolated from the calibration curve. In the Standard Addition Method, known quantities of the analyte are added to the samples and the increase in analytical response is measured. When the analytical response is linearly related to concentration, the concentration of the unknown analyte can be found by plotting the analytical response from a series of standards and extrapolating the unknown concentration from the curve. In this graph, however, the x-axis is the concentration of added analyte after being mixed with the sample. The x-intercept of the curve is the concentration of the unknown following dilution. The primary advantage of the standard addition method is that the matrix remains constant for all samples.

While the Standard Addition Method is used specifically for quantitative analysis, the Chemical Imaging Addition Method can be used for qualitative and quantitative analysis. The Chemical Imaging Addition Method relies upon spatially isolating analyte standards in order to calibrate the Chemical Imaging analysis. In chemical imaging, thousands of linearly independent, spatially-resolved spectra are collected in parallel of analytes found within complex host matrices. These spectra can then be processed to generate unique contrast intrinsic to analyte species without the use of stains, dyes, or contrast agents. Various spectroscopic methods including near-infrared (NIR) absorption spectroscopy can be used to probe molecular composition and structure without being destructive to the sample. Similarly, in NIR chemical imaging the contrast that is generated reveals the spatial distribution of properties revealed in the underlying NIR spectra.

The Chemical Imaging Addition Method can involve several data processing steps, typically including, but not limited to:

1. Ratiometric correction in which the sample NIR image is divided by the background NIR image to produce a result having a floating point data type.
2. The divided image is normalized by dividing each intensity value at every pixel in the image by the vector norm for its corresponding pixel spectrum. Where the vector norm is the square root of the sum of the squares of pixel intensity values for each pixel spectrum. Normalization is applied for qualitative analysis of NIR chemical images. For quantitative analysis, normalization is not employed, but relies instead on the use of partial least squares regression (PLSR) techniques.
3. Correlation analysis, including Euclidian Distance and Cosine correlation analysis (CCA) are established multivariate image analysis techniques that assess similarity in spectral image data while simultaneously suppressing background effects. More specifically, CCA assesses chemical heterogeneity without the need for training sets, identifies differences in spectral shape and efficiently provides chemical image based contrast that is independent of absolute intensity. The CCA algorithm treats each pixel spectrum as a projected vector in n-dimensional space, where n is the number of wavelengths sampled in the image. An orthonormal basis set of vectors is chosen as the set of reference vectors and the cosine of the angles between each pixel spectrum vector and the reference vectors are calculated. The intensity values displayed in the resulting CCA images are these cosine values, where a cosine value of 1 indicates the pixel spectrum and reference spectrum are identical, and a cosine value of 0 indicates the pixel spectrum and the reference spectrum are orthogonal (no correlation). The dimensions of the resulting CCA image is the same as the original image because the orthonormal basis set provides n reference vectors, resulting in n CCA images.
4. Principal component analysis (PCA) is a data space dimensionality reduction technique. A least squares fit is drawn through the maximum variance in the n-dimensional dataset. The vector resulting from this least squares fit is termed the first principal component (PC) or the first loading. After subtracting the variance explained from the first PC, the operation is repeated and the second principal component is calculated. This process is repeated until some percentage of the total variance in the data space is explained (normally 95% or greater). PC Score images can then be visualized to reveal orthogonal information including sample information, as well as instrument response, including noise. Reconstruction of spectral dimension data can then be performed guided by cluster analysis, including without PCs that describe material or instrument parameters that one desires to amplify or suppress, depending on the needs of the sensing application.

Figure 2:
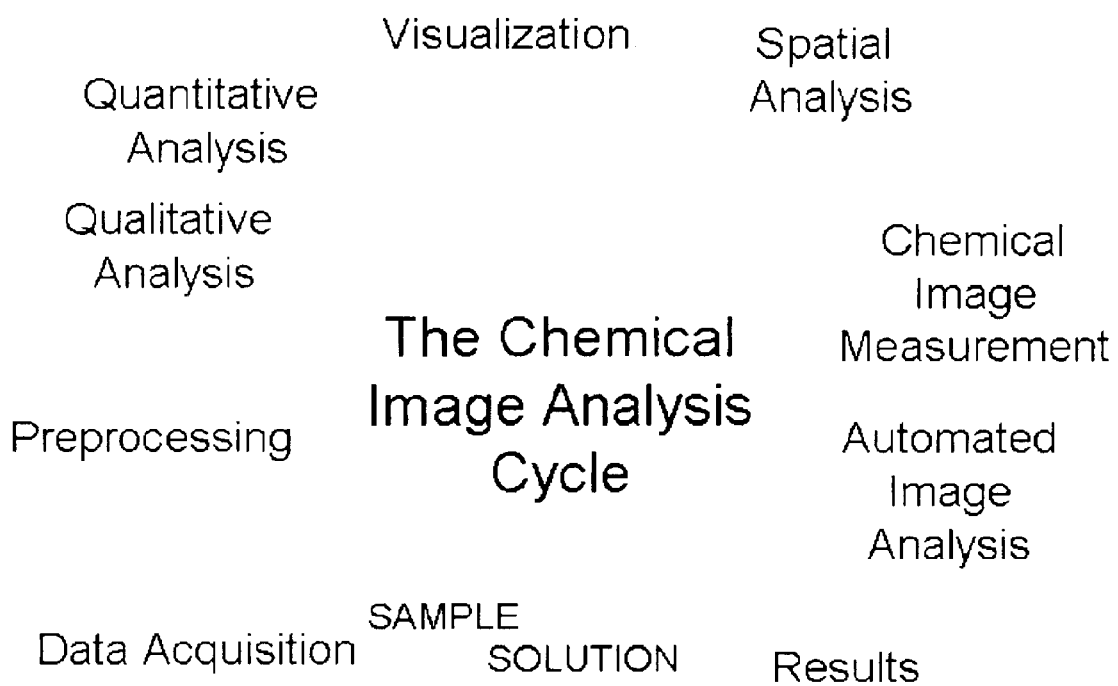
FIG. 2 shows a diagram of the chemical imaging data analysis cycle performed in software.

Effective materials characterization with the disclosed NIR chemical imaging microscope invention typically requires application of a multitude of software procedures to the NIR chemical image. A schematic of the chemical image analysis cycle is shown in FIG. 2. A fairly comprehensive description of the variety of steps used to process chemical images is described below.

Until recently, seamless integration of spectral analysis, chemometric analysis and digital image analysis has not been commercially available. Individual communities have independently developed advanced software applicable to their specific requirements. For example, digital imaging software packages that treat single-frame gray-scale images and spectral processing programs that apply chemometric techniques have both reached a relatively mature state. One limitation to the development of chemical imaging, however, has been the lack of integrated software that combines enough of the features of each of these individual disciplines to have practical utility.

Historically, practitioners of chemical imaging were forced to develop their own software routines to perform each of the key steps of the data analysis. Typically, routines were prototyped using packages that supported scripting capability, such as Matlab, IDL, Grams or LabView. These packages, while flexible, are limited by steep learning curves, computational inefficiencies, and the need for individual practitioners to develop their own graphical user interface (GUI). Today, commercially available software does exist that provides efficient data processing and the ease of use of a simple GUI.

Software that meets these goals must address the entirety of the chemical imaging process. The chemical imaging analysis cycle illustrates the steps needed to successfully extract information from chemical images and to tap the full potential provided by chemical imaging systems. The cycle begins with the selection of sample measurement strategies and continues through to the presentation of a measurement solution. The first step is the collection of images. The related software must accommodate the full complement of chemical image acquisition configurations, including support of various spectroscopic techniques, the associated spectrometers and imaging detectors, and the sampling flexibility required by differing sample sizes and collection times. Ideally, even relatively disparate instrument designs can have one intuitive GUI to facilitate ease of use and ease of adoption.

The second step in the analysis cycle is data preprocessing. In general, preprocessing steps attempt to minimize contributions from chemical imaging instrument response that are not related to variations in the chemical composition of the imaged sample. Some of the functionalities needed include: correction for detector response, including variations in detector quantum efficiency, bad detector pixels and cosmic events; variation in source illumination intensity across the sample; and gross differentiation between spectral lineshapes based on baseline fitting and subtraction. Examples of tools available for preprocessing include ratiometric correction of detector pixel response; spectral operations such as Fourier filters and other spectral filters, normalization, mean centering, baseline correction, and smoothing; spatial operations such as cosmic filtering, low-pass filters, high-pass filters, and a number of other spatial filters.

Once instrument response has been suppressed, qualitative processing can be employed. Qualitative chemical image analysis attempts to address a simple question, "What is present and how is it distributed?". Many chemometric tools fall under this category. A partial list includes: correlation techniques such as cosine correlation and Euclidean distance correlation; classification techniques such as principal components analysis, cluster analysis, discriminant analysis, and multi-way analysis; and spectral deconvolution techniques such as SIMPLISMA, linear spectral unmixing and multivariate curve resolution.

Quantitative analysis deals with the development of concentration map images. Just as in quantitative spectral analysis, a number of multivariate chemometric techniques can be used to build the calibration models. In applying quantitative chemical imaging, all of the challenges experienced in non-imaging spectral analysis are present in quantitative chemical imaging, such as the selection of the calibration set and the verification of the model. However, in chemical imaging additional challenges exist, such as variations in sample thickness and the variability of multiple detector elements, to name a few. Depending on the quality of the models developed, the results can range from semi-quantitative concentration maps to rigorous quantitative measurements.

Results obtained from preprocessing, qualitative analysis and quantitative analysis must be visualized. Software tools must provide scaling, automapping, pseudo-color image representation, surface maps, volumetric representation, and multiple modes of presentation such as single image frame views, montage views, and animation of multidimensional chemical images, as well as a variety of digital image analysis algorithms for look up table (LUT) manipulation and contrast enhancement.

Once digital chemical images have been generated, traditional digital image analysis can be applied. For example, Spatial Analysis and Chemical Image Measurement involve binarization of the high bit depth (typically 32 bits/pixel) chemical image using threshold and segmentation strategies. Once binary images have been generated, analysis tools can examine a number of image domain features such as size, location, alignment, shape factors, domain count, domain density, and classification of domains based on any of the selected features. Results of these calculations can be used to develop key quantitative image parameters that can be used to characterize materials.

The final category of tools, Automated Image Processing, involves the automation of key steps or of the entire chemical image analysis process. For example, the detection of well defined features in an image can be completely automated and the results of these automated analyses can be tabulated based on any number of criteria (particle size, shape, chemical composition, etc). Automated chemical imaging platforms have been developed that can run for hours in an unsupervised fashion.

This invention incorporates a comprehensive analysis approach that allows user's to carefully plan experiments and optimize instrument parameters and should allow the maximum amount of information to be extracted from chemical images so that the user can make intelligent decisions.

EXAMPLE

Overview

As the demand for high quality, low cost X-ray, γ-ray and imaging detector devices increases, there is a need to improve the quality and production yield of semiconductor materials used in these devices. One effective strategy for improving semiconductor device yield is through the use of better device characterization tools that can rapidly and nondestructively identify defects at early stages in the fabrication process. Early screening helps to elucidate the underlying causes of defects and to reduce downstream costs associated with processing defect laden materials that are ultimately scrapped. The present invention can be used to characterize tellurium inclusion defects in cadmium zinc telluride (CdZnTe) semiconductor materials based on near infrared imaging. With this approach, large area wafers can be inspected rapidly and non-destructively in two and three spatial dimensions by collecting NIR image frames at multiple regions of interest throughout the wafer using an automated NIR imaging system. The NIR image frames are subjected to image processing algorithms including background correction and image binarization. Particle analysis is performed on the binarized images to reveal tellurium inclusion statistics, sufficient to pass or fail wafers. In addition, data visualization software is used to view the tellurium inclusions in two and three spatial dimensions.

Background

The present invention has been used to automatically inspect tellurium inclusions in CdZnTe. Compound semiconductors are challenging to fabricate. There are several steps along the manufacturing process in which defects can arise. The chemical nature associated with semiconductor defects often plays a vital role in device performance. Device fabrication and device processing defects can be difficult and time consuming to measure during manufacturing. Unfortunately, defective devices are often left undiagnosed until latter stages in the manufacturing process because of the inadequacy of the metrology tools being used. This results in low production yields and high costs which can be an impediment to growth in the semiconductor device market potential.

There is a general need in the semiconductor industry for metrology technologies that can nondestructively assess semiconductor material defects and ultimately increase manufacturing yields. A potential solution is to develop a high throughput screening system capable of fusing multiple chemical imaging modalities into a single instrument. Chemical imaging combines digital imaging and molecular spectroscopy for the chemical analysis of materials. A modality of based on near-infrared (NIR) chemical imaging can be used to inspect tellurium inclusions in CdZnTe compound semiconductor materials.

CdZnTe is a leading material for use in room temperature X-ray detectors, γ-ray radiation detectors and imaging devices. Applications for these devices include nuclear diagnostics, digital radiography, high-resolution astrophysical X-ray and γ-ray imaging, industrial web gauging and nuclear nonproliferation. These devices are often decorated with microscopic and macroscopic defects limiting the yield of large-size, high-quality materials. Defects commonly found in these materials include cracks, grain boundaries, twin boundaries, pipes, precipitates and inclusions. CdZnTe wafers are often graded based on the size and number of Te inclusion defects present.

The definition used by Rudolph and Muhlberg for tellurium inclusions (i.e., tellurium-rich domains in the 1–50 $\mu$m size range that originate as a result of morphological instabilities at the growth interface as tellurium-rich melt droplets are captured from the boundary layer ahead of the interface) has been adopted and is used herein. There have been numerous studies on the composition and distribution of tellurium inclusions in CdZnTe material. It has been demonstrated that the presence of tellurium inclusions can impair the electronic properties of CdZnTe materials— consequently degrading the end-product device performance.

The current procedure used by low volume semiconductor manufacturers for characterizing tellurium inclusions in CdZnTe is labor intensive, susceptible to human error and provides little information on inclusions in the 1–5 $\mu$m size scale. Inclusions are viewed and counted manually by a human operator using an IR microscope platform. When an inclusion is identified that is suspected to exceed a specified size limit, a Polaroid film photograph is taken. An overlay of a stage micrometer is laid over the photograph to determine the size. This analysis is relatively time consuming, often taking several minutes to characterize a region of interest from a large wafer.

The present invention can be used for automated characterization of microscale tellurium inclusions in CdZnTe based on volumetric NIR chemical imaging. The system takes advantage of the fact that CdZnTe is transparent to infrared wavelengths (>850 nm). When viewing CdZnTe with an infrared focal plane array (IR-FPA) through a NIR LC imaging spectrometer, tellurium inclusions appear as dark, absorbing domains. The invention images wafers in two and three spatial dimensions capturing raw infrared images at each region of interest. Images are automatically background equilibrated, binarized and processed. The processed data provides particle statistical information such as inclusion counts, sizes, density, area and shape. The system provides a rapid method for characterizing tellurium inclusions as small as 0.5 $\mu$m while virtually eliminating the subjectivity associated with manual inspection.

Sample Description

Tellurium-rich CdZnTe samples were produced by a commercial supplier (eV Products) for analysis. Samples containing high tellurium inclusion densities were purposely acquired to effectively demonstrate the capabilities of the automated tellurium inclusions mapping system. The CdZnTe materials were grown by the Horizontal Bridgeman (HB) method and contained a nominal zinc cation loading concentration of 4% and an average etch pit density of $4 \times 10^4/cm^2$. The materials displayed a face A <111> orientation and were polished on both sides. Sample thicknesses ranged from approximately 1 mm to 15 mm. No further sample preparation was necessary for the automated tellurium inclusion mapping analysis.

Data Collection

Volumetric maps of the tellurium inclusions in the CdZnTe samples were obtained by first placing the sample on the XYZ-translational stage of the automated mapping system. NIR image frames were then captured through the LC imaging spectrometer at a wavelength that maximized the Te precipitate contrast relative to the surrounding CdZnTe matrix in the X-Y direction at multiple regions of interest across the samples. Depth profiling was achieved by translating the sample focus under the microscope at user-defined increments. This process was then repeated in an iterative fashion until the entire wafer was characterized.

Data Processing

Once imaging data was collected, ChemImage was used to process the data. For each wafer, the software generates a background-corrected grayscale image, a binarized image using the threshold value selected for each frame of the image, a montage view of the binarized image and particle statistics. The particle statistics table includes information such as particle counts, particle sizes, particles densities, and a number of geometrical parameters such as particle area and particle aspect ratios.

NIR Imaging

Figures 3, 4:
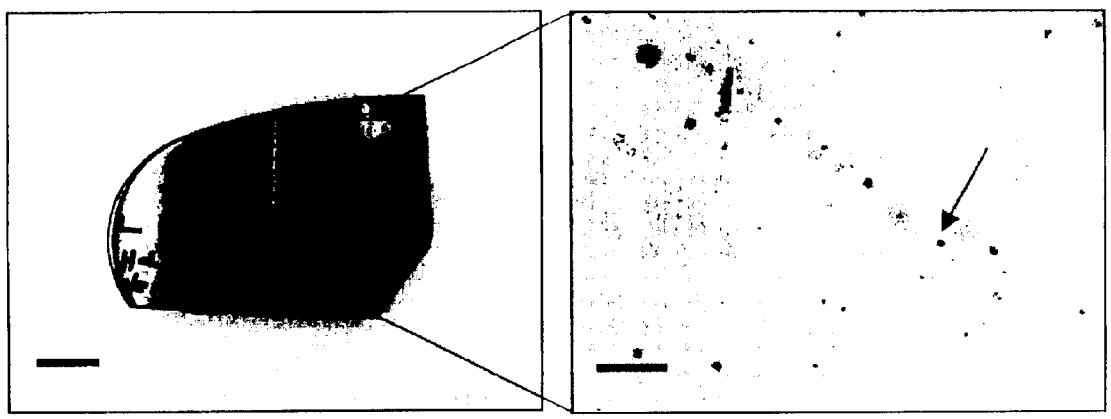
FIG. 3 is a digital brightfield image of a CdZnTe semiconductor material decorated with tellurium inclusions.
FIG. 4 an NIR microscopic transmittance image of a CdZnTe semiconductor material decorated with tellurium inclusions.

FIGS. 3 and 4, respectively, show a digital macro brightfield image and a raw NIR microscopic transmittance image of a CdZnTe semiconductor material with numerous tellurium inclusions. The left half of the wafer has been polished. The tellurium inclusions appear as dark spots in the microscopic NIR image. The raw NIR microscopic image was acquired using the automated near-infrared tellurium inclusion volumetric mapping system.

Background Correction and Image Binarization

The automated particle analysis begins by applying a background correction preprocessing routine to the raw image frames. One of the biggest problems with the raw images collected is the gradually varying background across each image frame. As a result, a particle in one area of a frame may have a higher intensity value than the background of another area of that frame.

Figure 5A:
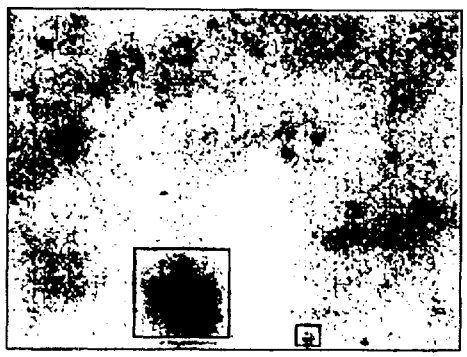
FIG. 5A illustrates a raw NIR image frame of a CdZnTe wafer sample.
Figure 5B:
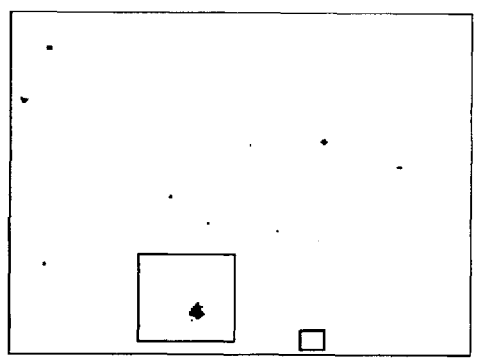
FIG. 5B illustrates an NIR image frame of the sample of FIG. 5A in which the threshold value for the image was set too low.
Figure 5C:
FIG. 5C illustrates an NIR image frame of the sample of FIG. 5A in which the threshold value for the image was set too high.
Figure 5D:
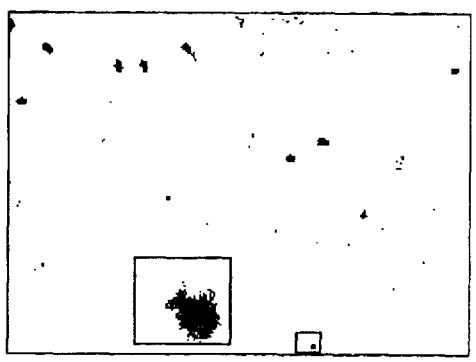
FIG. 5D illustrates an NIR image frame of the sample of FIG. 5A in which the threshold value for the image was set to an intermediate level.

FIGS. 5A–5D illustrate the difficulty associated with selecting a threshold value for an image with a widely varying background. In FIGS. 5A–5D, regions 1 and 2 have mean intensity values of approximately 2600 and 1950, respectively. The whole of region 1 is primarily a particle whereas region 2 is primarily background with a small particle in the center. FIG. 5A shows a raw NIR image frame collected from a single region of interest in a CdZnTe wafer. At wavelengths longer than approximately 850 nm, CdZnTe is transparent while tellurium inclusions remain opaque. A NIR image of the sample is light where there are no precipitates and dark where there are precipitates. In FIG. 5B, the threshold value is set low enough (value=1520) that the particle in region 2 is correctly identified, but most of the remaining particles are not found. In FIG. 5C, the threshold value is set high enough (value=2470) so that all particles are detected. Unfortunately, a large area of the frame is incorrectly identified as one very large particle. FIG. 5D displays the case in which the threshold is set to an intermediate value (value=1960). Many of the particles are correctly identified, but the particle in region 2 is identified as being larger than it actually is.

To address this issue, a background correction step is used to force the background to be essentially constant across a given image frame. The procedure applies a moving window across the image frame and smoothes the resulting background before subtracting it from the frame. Other operations such as low pass filtering and selective removal of bad camera pixels are also applied.

The second step in the automated particle analysis is the selection of the threshold value resulting in the binarized image which best reflects the number and size of particles actually present in the sample being imaged. A human operator would typically approach this problem by trying multiple threshold values and comparing the resulting binarized images to the actual image to see which binarized image best matches their perception of the particles in the actual image. The algorithm employed by the NIR chemical imaging microscope system takes essentially the same approach. A series of threshold values are used to generate binarized images. Each binarized image is submitted to a routine that finds the particles present in the image. A set of particle morphology rules was developed to determine the point at which the threshold value identifies the particles consistent with results obtained by a trained human operator. This threshold value is then further refined with using derivative operations.

Figure 6:
FIG. 6A is the original raw image of four adjacent regions of interest on a CdZnTe wafer.
FIG. 6B is the background-corrected image corresponding to the four adjacent regions of interest of the CdZnTe wafer of FIG. 6A.
FIG. 6C is the binarized image corresponding to the four adjacent regions of interest of the CdZnTe wafer of FIG. 6A.
Figure 6:
Figure 6:
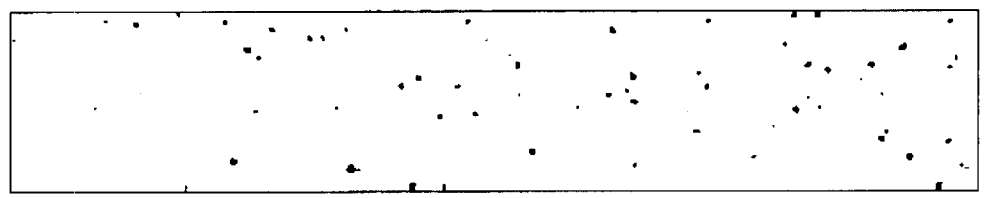

FIGS. 6A–6C show montage views of raw, background-corrected, and binarized NIR image frames, respectively, corresponding to four adjacent regions of interest from a CdZnTe wafer. A visual inspection of these images suggests that the particle analysis adequately identifies the particles in an automated fashion.

Volumetric Reconstruction and Visualization

It is of particular interest to the semiconductor manufacturing industry to view defects, including tellurium inclusions in this example, in a three dimensional volumetric view. Individual binarized image frames generated at discrete axial planes of focus have been reconstructed into a volumetric view allowing users to view tellurium inclusions in three-dimensional space.

Figure 7:
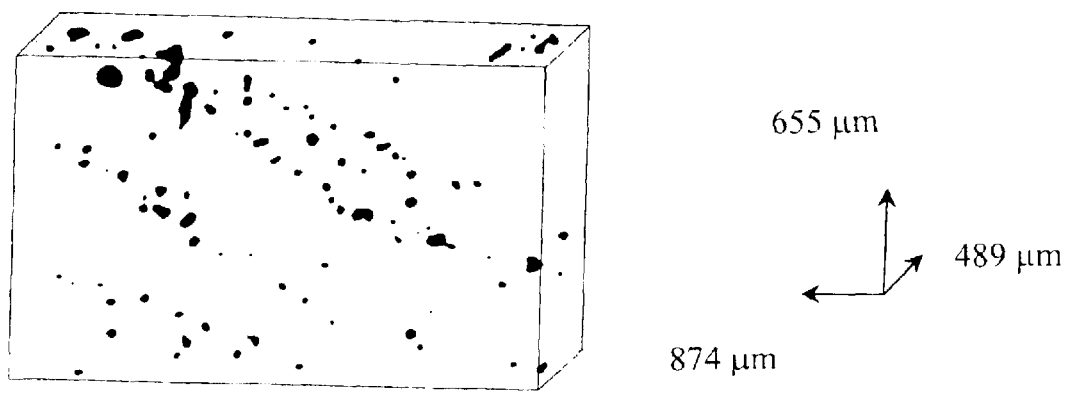
FIG. 7 is a three-dimensional view of tellurium inclusions in a CdZnTe wafer.

FIG. 7 shows a 3D volumetric view of tellurium inclusions in CdZnTe generated from 50 individual image slices. FIG. 7 is constructed using a nearest neighbors computational approach for volume reconstruction. Improved results can be obtained using more sophisticated strategies that deconvolve the entire image volume using iterative deconvolution approaches. The staring time of the sensor used to gather the volumetric data was less than 1 sec. The total acquisition time for the data generated in this figure was well under a minute. Note how the inclusions tend to form in planes described as veils. These veils are believed to be subgrain boundaries within the CdZnTe material. Grain boundaries provide low energy nucleation sites for the inclusions to form during the growth process.

Table 1 provides tabulated statistical information on the volumetric data shown in FIG. 7.

titative information about tellurium inclusions present in CdZnTe wafers in two and three spatial dimensions. This system boasts improved spatial resolution (~0.5 $\mu$m) compared to systems currently used by many semiconductor manufacturers and it virtually eliminates the subjectivity associated with human counting and sizing measurements. Whole wafers are capable of being characterized in minutes.

While in the above example, the present invention has been demonstrated in connection with the characterization of semiconductors, it is to be expressly understood that the present invention can also be used in the characterization of other materials including, but not limited to, food and agricultural products, paper products, pharmaceutical materials, polymers, thin films and in medical uses.

Although present preferred embodiments of the invention have been shown and described, it should be distinctly understood that the invention is not limited thereto but may be variously embodied within the scope of the following claims.

We claim:

1. A near infrared radiation chemical imaging system comprising:
    a) an illumination source for illuminating an area of a sample using light in the near infrared radiation wavelength;
    b) a device for collecting a spectrum of near infrared wavelength radiation light transmitted, reflected, emitted or scattered from said illuminated area of said sample and producing a collimated beam therefrom;
    c) a near infrared imaging spectrometer for selecting a near infrared radiation image of said collimated beam; and
    d) a detector for collecting said filtered near infrared images.

2. The system of claim 1 wherein said illumination source is one of a quartz tungsten halogen lamp, a tunable laser, a metal halide lamp, and a xenon arc lamp.

3. The system of claim 1 wherein said device for collecting is one of a refractive type infinity-corrected near infrared optimized microscope objective, a refractive fixed tube length microscope objective, and a reflecting microscope objective.

TABLE 1

| | Particle Statistics Slice Number and Depth ($\mu$m) | | | | | |
|---|---|---|---|---|---|---|
| Parameters | 0 (0) | 10 (89.77) | 20 (189.52) | 30 (289.26) | 40 (389.01) | 50 (488.75) |
| # of Inclusions | 25 | 30 | 27 | 24 | 25 | 36 |
| Mean Diameter ($\mu$m) | 12.12 | 11.38 | 12.75 | 15.70 | 12.89 | 13.73 |
| Density (Inclusions/cm$^2$) | 4368 | 5241 | 4717 | 4193 | 4368 | 6289 |
| Area ($\mu$m$^2$) | 97.48 | 73.78 | 91.67 | 119.25 | 96.29 | 98.15 |
| Perimeter ($\mu$m) | 40.40 | 37.32 | 43.27 | 50.72 | 41.93 | 43.98 |
| Shape Factor | 0.60 | 0.60 | 0.58 | 0.53 | 0.60 | 0.55 |
| Maximum Chord Length | 12.12 | 11.38 | 12.75 | 15.70 | 12.89 | 13.73 |
| Feret 1 Diameter | 9.17 | 9.56 | 11.33 | 12.64 | 10.48 | 10.16 |
| Feret 2 Diameter | 10.26 | 9.01 | 10.10 | 12.18 | 10.37 | 11.60 |
| Aspect Ratio | 1.02 | 1.19 | 1.16 | 1.08 | 1.02 | 0.95 |

Defects such as tellurium inclusions affect the electrical properties in CdZnTe semiconductor materials, degrading end-product device performance. Having the ability to rapidly and non-invasively identify and quantify tellurium inclusion defects at critical stages in the fabrication process provides semiconductor manufacturers with information that will enable them to optimize the manufacturing process and reduce production costs. The Automated NIR Volumetric Mapping System described here is capable of providing such information. The system provides qualitative and quan- 4. The system of claim 1 wherein said near infrared imaging spectrometer is selected from the group consisting of Lyot liquid crystal tunable filters; Evans Split-Element liquid crystal tunable filters; Solc liquid crystal tunable filters; Ferroelectric liquid crystal tunable filters; Liquid crystal Fabry Perot filters; a hybrid filter formed from a combination of liquid crystal tunable filters; and a combination of a liquid crystal tunable filter and a fixed bandpass and bandreject filters.

5. The system of claim 1 wherein said detector is a near infrared radiation focal plane array detector.

6. The system of claim 5 wherein said detector is selected from the group consisting of indium gallium arsenide, platinum silicide, indium antimonide, palladium silicide, indium germanide, and mercury cadmium telluride.

7. The system of claim 1 further comprising a visible wavelength imagery system.

8. The system of claim 7 wherein said visible imagery system comprises:
   a) an illumination source for illuminating an area of said sample using light in the visible optical wavelengths; and
   b) a device for detecting said visible wavelength light from said illuminated area of said sample.

9. The system of claim 8 wherein said device for detecting said visible wavelength light comprises an analog and digital detector based on at least one of a silicon charge-coupled device detector and a silicon CMOS detectors.

10. The system of claim 8 further comprising a processor for producing a near infrared radiation chemical image of said sample.

11. The system of claim 8 further comprising an algorithm for combining the near infrared and visible image data.

12. A chemical imaging system comprising:
   a) an illumination source for illuminating an area of a sample using light in the near infrared radiation wavelength and light in the visible wavelength;
   b) a device for collecting a spectrum of near infrared wavelength radiation light transmitted, reflected, emitted or scattered from said illuminated area of said sample and producing a collimated beam therefrom;
   c) a near infrared imaging spectrometer for selecting a near infrared radiation image of said collimated beam;
   d) detector for collecting said filtered near infrared images; and
   e) a device for detecting said visible wavelength light from said illuminated area of said sample.

13. A chemical imaging method comprising the steps of:
   a) illuminating an area of a sample using light in the near infrared radiation wavelength and light in the visible wavelength;
   b) collecting a spectrum of near infrared wavelength radiation light transmitted, reflected, emitted or scattered from said illuminated area of said sample and producing a collimated beam therefrom;
   c) filtering said collimated beam to produce a near infrared radiation image of said collimated beam while simultaneously detecting said optical wavelength light from said illuminated area of said sample;
   d) collecting said filtered near infrared images; and
   e) processing said collected near infrared images to produce a chemical image of said sample.

14. A method for producing a volumetric image of a sample comprising the steps of:
   a) incorporating a refractive image formation optic exhibiting a chromatic response in the optical path of the microscope before the near infrared detector;
   b) collecting images of said sample at a plurality of near infrared wavelengths through said objective at a fixed focus condition; and
   c) processing said collected images to reconstruct a depth resolved image of said sample.

15. A method for chemically analyzing a sample comprising the steps of:
   a) seeding said sample with a plurality of analytes having at least one of a known composition, structure and concentration;
   b) collecting a plurality of spatially-resolved spectra for said plurality of analytes;
   c) producing a plurality of chemical images of said sample containing said plurality of anayltes; and
   d) processing said plurality of chemical images to generate a chemical image of said sample.

16. The method of claim 15 wherein said processing step comprises at least one of:
   a) correcting the image by dividing a near infrared image of said sample by a near infrared image of a background of said image to produce a resulting ratioed image;
   b) normalizing the divided image by dividing each intensity value at every pixel in the image by the vector norm for its corresponding pixel spectrum, said vector norm being the square root of the sum of the squares of pixel intensity values for each pixel spectrum;
   c) processing said image using a cosine correlation analysis method wherein each pixel spectrum is treated as a projected vector in n-dimensional space, wherein n is the number of wavelengths sampled in the image; and
   d) processing said image using a principal component analysis method wherein a least squares fit is drawn through the maximum variance in the n-dimensional dataset.

* * * * *